US009956429B2

(12) United States Patent
Holmes et al.

(10) Patent No.: US 9,956,429 B2
(45) Date of Patent: May 1, 2018

(54) METHOD AND SYSTEM FOR AUTOMATED EVALUATION OF MULTIPLE PORTAL DOSE IMAGES IN RADIATION THERAPY

(75) Inventors: Todd G. Holmes, Bethlehem, CA (US); David Kleiner, Zurich (CH)

(73) Assignees: VARIAN MEDICAL SYSTEMS INTERNATIONAL AG, Zug (CH); VARIAN MEDICAL SYSTEMS, INC., Palo Alto, CA (US)

( * ) Notice: Subject to any disclaimer, the term of this patent is extended or adjusted under 35 U.S.C. 154(b) by 726 days.

(21) Appl. No.: 13/073,390

(22) Filed: Mar. 28, 2011

(65) Prior Publication Data

US 2012/0250971 A1 Oct. 4, 2012

(51) Int. Cl.
*A61N 5/10* (2006.01)
*G06F 19/00* (2011.01)

(52) U.S. Cl.
CPC ......... *A61N 5/1048* (2013.01); *A61N 5/1071* (2013.01); *G06F 19/3481* (2013.01); *A61N 2005/1054* (2013.01)

(58) Field of Classification Search
CPC ................ A61N 5/1048; A61N 5/1071; A61N 2005/1054; G06F 19/3481
See application file for complete search history.

(56) References Cited

U.S. PATENT DOCUMENTS

| 6,618,620 | B1 * | 9/2003 | Freundlich et al. | 607/27 |
| 7,289,599 | B2 * | 10/2007 | Seppi et al. | 378/65 |
| 7,327,902 | B2 * | 2/2008 | Ritt et al. | 382/294 |
| 7,611,452 | B2 * | 11/2009 | Allison et al. | 600/1 |
| 7,773,788 | B2 * | 8/2010 | Lu et al. | 382/128 |
| 7,945,022 | B2 * | 5/2011 | Nelms et al. | 378/65 |
| 8,095,203 | B2 * | 1/2012 | Wright et al. | 600/426 |
| 8,180,020 | B2 * | 5/2012 | Kilby et al. | 378/65 |
| 8,437,449 | B2 * | 5/2013 | Riley et al. | 378/65 |
| 8,442,287 | B2 * | 5/2013 | Fordyce et al. | 382/128 |
| 2004/0068182 | A1 * | 4/2004 | Misra | A61N 5/1049 600/427 |

(Continued)

OTHER PUBLICATIONS

Cilla et al., "Comparison of measured and computed portal dose for IMRT treatment", Jouranal of Applied Clinical Medical Physics, vol. 7, No. 3, 2006, 65-79.*

(Continued)

*Primary Examiner* — Katrina Fujita
(74) *Attorney, Agent, or Firm* — Vista IP Law Group, LLP

(57) ABSTRACT

A method of evaluating a portal dose image includes obtaining a template from a database, the template prescribing one or more evaluation criteria, receiving a first portal dose image, and using a processor to evaluate the first portal dose image based at least in part on the one or more evaluation criteria from the template. In some embodiments, a second image is automatically evaluated after the first image is evaluated. A system for evaluating a portal dose image includes a processor that is communicatively coupled to a database, the database having a template that prescribes one or more evaluation criteria, wherein the processor is configured to obtain the template from the database, receive a first portal dose image, and evaluate the first portal dose image based at least in part on the one or more evaluation criteria from the template.

62 Claims, 12 Drawing Sheets

(56) References Cited

U.S. PATENT DOCUMENTS

| | | | | |
|---|---|---|---|---|
| 2005/0111621 | A1* | 5/2005 | Riker | A61N 5/1031 378/65 |
| 2005/0151071 | A1* | 7/2005 | Nilsson | A61N 5/1048 250/252.1 |
| 2006/0078086 | A1* | 4/2006 | Riley et al. | 378/65 |
| 2006/0100509 | A1* | 5/2006 | Wright et al. | 600/426 |
| 2006/0193437 | A1* | 8/2006 | Boeing | A61B 6/032 378/115 |
| 2007/0088573 | A1* | 4/2007 | Ruchala | A61N 5/103 705/2 |
| 2007/0127623 | A1* | 6/2007 | Goldman | A61N 5/1031 378/65 |
| 2008/0269568 | A1* | 10/2008 | Lewis et al. | 600/300 |
| 2010/0082294 | A1* | 4/2010 | Adnani | A61N 5/10 702/182 |
| 2010/0104068 | A1* | 4/2010 | Kilby | A61N 5/1031 378/65 |
| 2010/0183121 | A1* | 7/2010 | Riker | A61N 5/1031 378/65 |
| 2011/0112863 | A1* | 5/2011 | Gogineni et al. | 705/3 |
| 2011/0191085 | A1* | 8/2011 | Jaffray | G06G 7/60 703/11 |
| 2012/0136677 | A1* | 5/2012 | Ziegenhein | A61N 5/1031 705/2 |
| 2016/0125602 | A1* | 5/2016 | Winfield | A61N 5/1071 382/132 |

OTHER PUBLICATIONS

Sharma et al., "Portal dosimetry for pretreatment verification of IMRT plan: a comparison with 2D ion chamber array", Jouranal of Applied Clinical Medical Physics, vol. 11, No. 4, 2010, 238-248.* van Elmpt et al., "A Monte Carlo based three-dimensional dose reconstruction method derived from portal dose images", Medical Physics 33, 2006, 2426-2434.* van Esch et al., "The use of an aSi-based EPID for routine absolute dosimetric pre-treatment verification of dynamic IMRT fields", Radiotherapy and Oncology 71, 2004, 223-234.*

Depuydt et al. "A quantitative evaluation of IMRT dose distributions: refinement and clinical assessment of the gamma evaluation." Radiotherapy and Oncology 62.3 (2002): 309-319.*

Korreman et al. "Dosimetric verification of RapidArc treatment delivery." Acta oncologica 48.2 (2009): 185-191.*

Low D.A., Harms W.B., Mutic S., Purdy J.A., "A technique for the quantitative evaluation of dose distributions", Med. Phys. 25 (5), 656-661, May 1998.

* cited by examiner

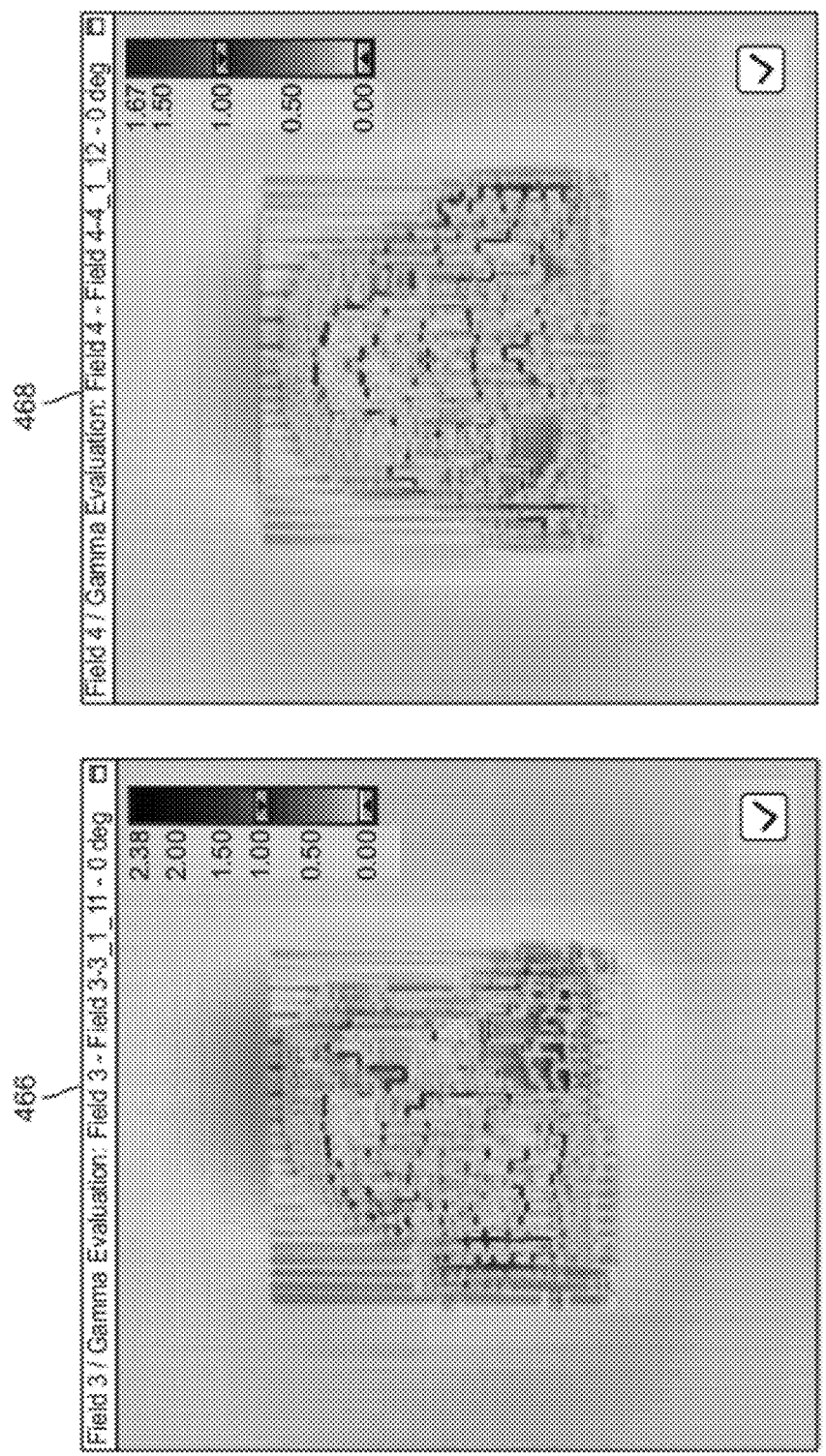
FIG. 4 (Cont. 1)

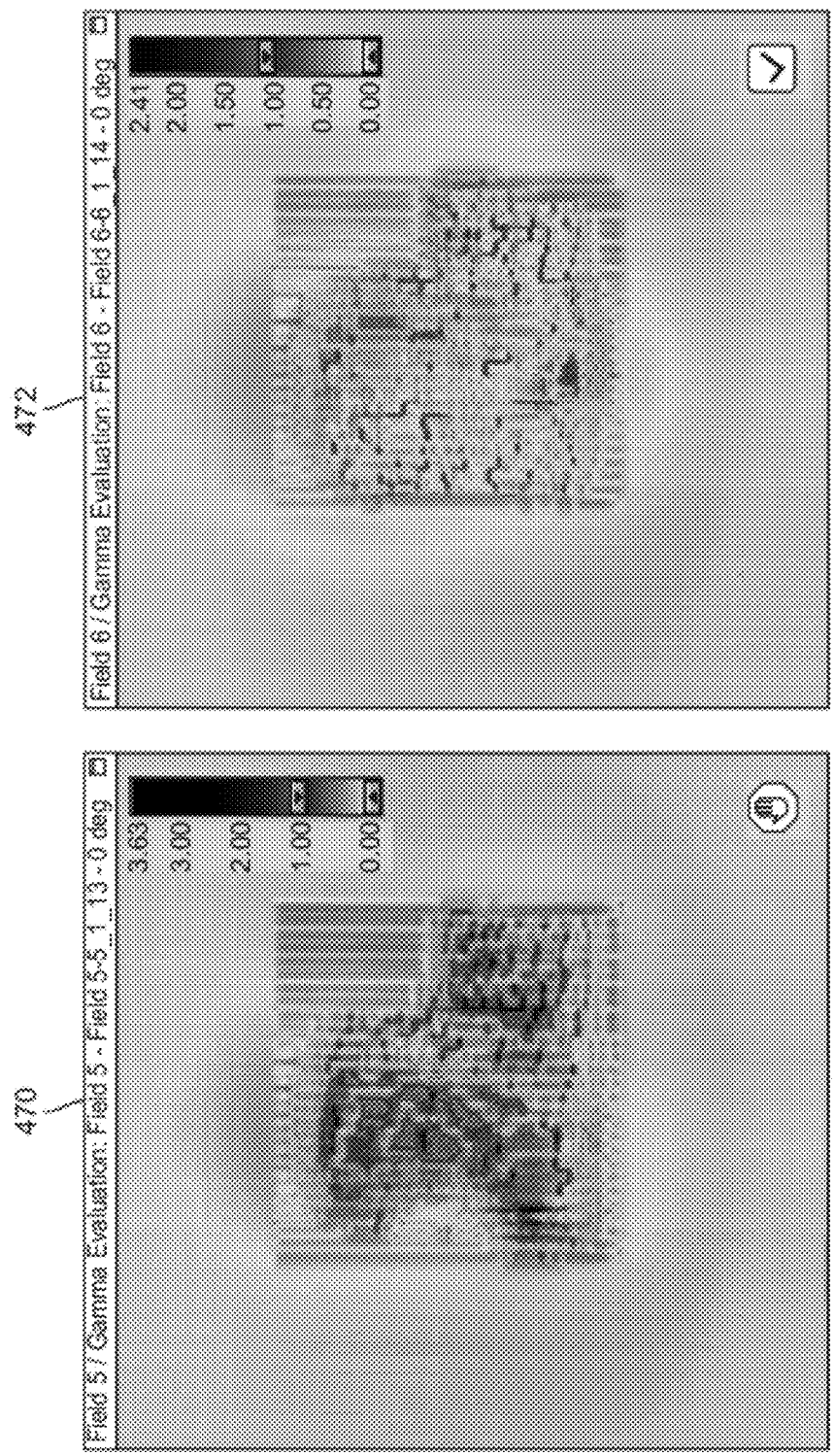
FIG. 4 (Cont. 2)

| Test | Value | Tol. |
|---|---|---|
| Area Gamma < 1.0 | 99.5 % | 97.0 % |
| Maximum Gamma | 1.82 | 2.00 |
| Average Gamma | 0.20 | 0.50 |
| Area Gamma > 0.8 | 1.2 % | 10.0 % |
| Area Gamma > 1.2 | 0.2 % | 1.0 % |

[Gamma DTA : 3.0 mm Tol. : 3.0 %]

| Test | Value | Tol. |
|---|---|---|
| Max. Dose Difference | 18.0 % | |
| Avg. Dose Difference | 1.0 % | |
| Area Dose Diff > 5.0 % | 2.4 % | 2.0 % |
| Area Dose Diff > 1.5 % | 20.4 % | 10.0 % |

| Field | |
|---|---|
| Analysis done by | DemoUser |
| Analysis Date | Thursday, July 08, 2010 5:48 PM |
| Normalization Method | Maximum of Each Dose |
| Portal Dose ID | Field 3-3_1_11 |
| Reference Dose ID | Field 3 |
| Analysis Result | Passed |

Detailed test results :

| Test | Value | Tol. |
|---|---|---|
| Area Gamma < 1.0 | 99.5 % | 97.0 % |
| Maximum Gamma | 1.84 | 2.00 |
| Average Gamma | 0.19 | 0.50 |
| Area Gamma > 0.8 | 1.2 % | 10.0 % |
| Area Gamma > 1.2 | 0.2 % | 1.0 % |

[Gamma DTA : 3.0 mm Tol. : 3.0 %]

| Test | Value | Tol. |
|---|---|---|
| Max. Dose Difference | 24.5 % | |
| Avg. Dose Difference | 1.0 % | |
| Area Dose Diff > 5.0 % | 2.3 % | 2.0 % |
| Area Dose Diff > 1.5 % | 19.6 % | 10.0 % |

Thursday, July 08, 2010 5:50:51 PM          Page 1 of 3

FIG. 5A (Cont.)

Applying the Template (Offline) — 606

| Portal Dose Images | | Predicted Dose: Field 1 - 10-Aug-2006 11:1 |
|---|---|---|

Plan: C1/7F HN mss1

Field | Session — 604

602 — Sat 12-Aug-2006 17:25
- ☐ Field 1-1_1_9 — Apply Template to Session ▶ | Default
  - ☑ Analysis: Mon 27-Oct-2008 | Test
- ☐ Field 2-2_1_10 | TestAbsolute — 600
  - ☑ Analysis: Mon 27-Oct-2008 | Test2
- ☐ Field 3-3_1_11
  - ☑ Analysis: Mon 27-Oct-2008
- ☐ Field 4-4_1_12
  - ☑ Analysis: Mon 27-Oct-2008

⬇ 620

Summary of Portal Dose Image Analyses

Session: Sat 12-Aug-2006 17:25

| Field | Image | Result |
|---|---|---|
| ☑ Field 1 | Field 1-1_1_9 | Passed |
| ☑ Field 2 | Field 2-2_1_10 | Passed |
| ☑ Field 3 | Field 3-3_1_11 | Passed |
| ⬤ Field 4 | Field 4-4_1_12 | Failed |
| ⬤ Field 5 | Field 5-5_1_13 | Failed |
| ⬤ Field 6 | Field 6-6_1_14 | Failed |
| ⬤ Field 7 | Field 7-7_1_15 | Failed |

⬤ Summary result of evaluation failed

Click on one of the images in the list to view the detailed analysis

[ Print Report... ]  [ Cancel & Delete Analyses ]  [ Close ]

FIG. 6

METHOD AND SYSTEM FOR AUTOMATED EVALUATION OF MULTIPLE PORTAL DOSE IMAGES IN RADIATION THERAPY

FIELD

This application relates generally to radiation therapy, and more particularly, to evaluation of dose images in radiation therapy.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Generally, a radiation treatment plan is determined before the radiation therapy is performed. In some cases, the dose of the radiation treatment plan is also evaluated before the treatment plan is carried out. Such dose evaluation may be performed by comparing a predicted dose of the treatment plan with a portal dose that is obtained based on an evaluation plan. This allows an accurate and precise dosage of radiation to be delivered to a patient.

Sometimes, a radiation treatment plan includes multiple fields. Existing techniques for evaluating doses of such radiation treatment plan involve analyzing each of the fields of the treatment plan. In such techniques, each of the fields of the treatment plan is analyzed manually with the aid of a computer. In particular, the user would manually input parameters to perform a test that compares predicted dose with portal dose. The user then manually analyzes the test result. In some cases, if the same test needs to be run again using different values of the parameters, the user would need to manually change the parameters, and rerun the test. Also, if additional test is needed, the user would again manually input parameters to perform another test to compare the predicted dose with the portal dose. Then the user again manually analyzes the additional test result. Such non-template based dose evaluation approach has been a standard procedure in radiation plan verification.

Applicant of the subject application determines that the standard procedure for performing dose evaluation on multiple fields of a treatment plan is repetitive and time consuming with many steps always being the same. Applicant also determines that manually changing values of the parameters to run the same test using the different parameter values is tedious and inefficient. Applicant therefore determines that it would be desirable to have a more efficient system and method for performing dose evaluation for radiation treatment plan, such as an intensity modulated radiation treatment (IMRT) plan.

SUMMARY

In accordance with some embodiments, a method of evaluating a portal dose image includes obtaining a template from a database, the template prescribing one or more evaluation criteria, receiving a first portal dose image, and using a processor to evaluate the first portal dose image based at least in part on the one or more evaluation criteria from the template.

In accordance with other embodiments, a system for evaluating a portal dose image includes a processor that is communicatively coupled to a database, the database having a template that prescribes one or more evaluation criteria, wherein the processor is configured to obtain the template from the database, receive a first portal dose image, and evaluate the first portal dose image based at least in part on the one or more evaluation criteria from the template.

In accordance with other embodiments, a computer product having a volatile or non-volatile medium that stores a set of instruction, an execution of which by a processor causes a process for evaluating a portal dose image to be performed, the process includes obtaining a template from a database, the template prescribing one or more evaluation criteria, receiving a first portal dose image, and using a processor to evaluate the first portal dose image based at least in part on the one or more evaluation criteria from the template.

In accordance with other embodiments, an apparatus for use in a process to evaluate dose image includes a screen displaying an user interface, wherein the user interface includes a plurality of fields for allowing a user to input evaluation criteria for evaluating one or more portal dose images, wherein the user interface also includes a save button for allowing the user to save the evaluation criteria as a template.

Other and further aspects and features will be evident from reading the following detailed description of the embodiments, which are intended to illustrate, not limit, the invention.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 6 illustrates a user interface for applying template for dose evaluation offline in accordance with some embodiments.

DESCRIPTION OF THE EMBODIMENTS

Figure 1:
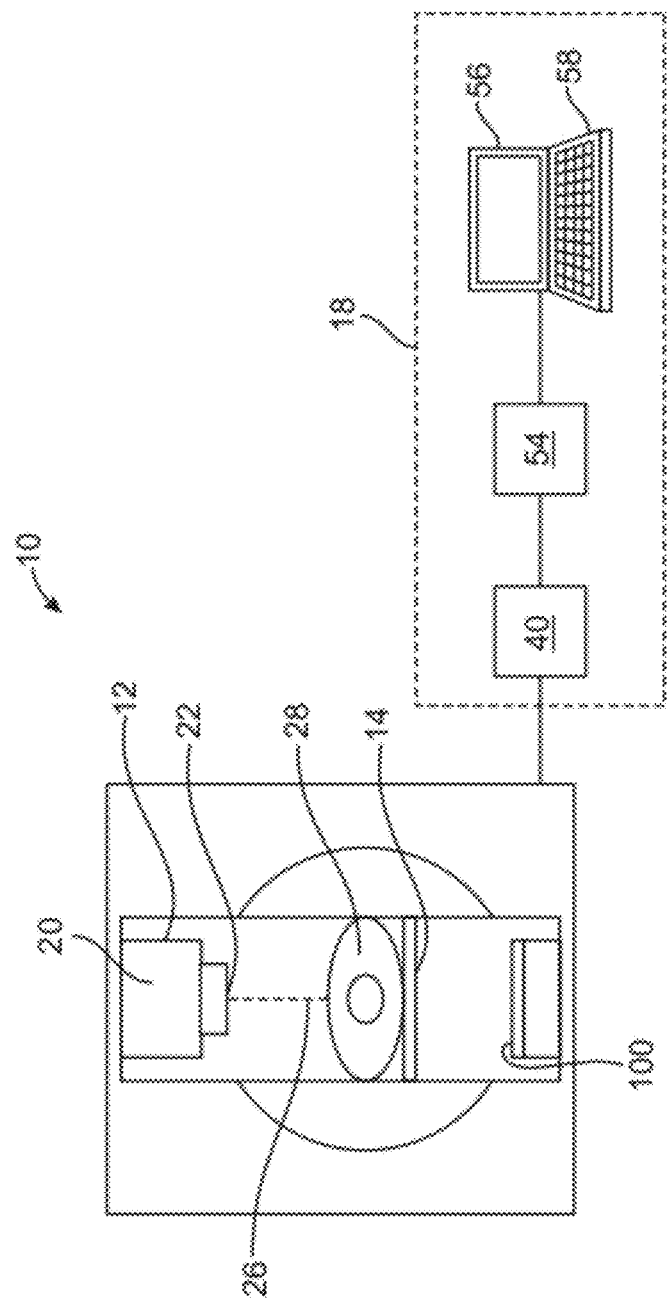
FIG. 1 illustrates a system for delivering radiation in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a radiation treatment system 10 for delivering radiation in accordance with a treatment plan that is determined using techniques described herein. The system 10 includes a gantry 12 (in the form of an arm), a patient support 14 for supporting a patient, and a control system 18 for controlling an operation of the gantry 12. The system 10 also includes a radiation source 20 that projects a beam 26 of radiation towards a patient 28 while the patient 28 is supported on support 14, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In such cases, the system 10 will include an imager, such as the imager 100, located at an operative position relative to the source 20 (e.g., under the support 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In further embodiments, the radiation source 20 can be a diagnostic radiation source. In the illustrated embodiments, the radiation source 20 is coupled to the arm gantry 12. Alternatively, the radiation source 20 may be located within a bore, and may be coupled to a ring gantry.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 28, and during a treatment procedure, the gantry 12 rotates about the patient 28 (as in an arc-therapy). In other embodiments, the gantry 12 does not rotate about the patient 28 during a treatment procedure. In such case, the gantry 12 may be fixed, and the patient support 14 is rotatable. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. Further, the radiation source 20 is not limited to delivering treatment energy in the form of x-ray, and may deliver other types of radiation energy. For example, in other embodiments, the radiation source 20 may be a proton source for delivering protons to treat patient, or other types of particle source for delivering other types of particles for treating patient.

Figure 2:
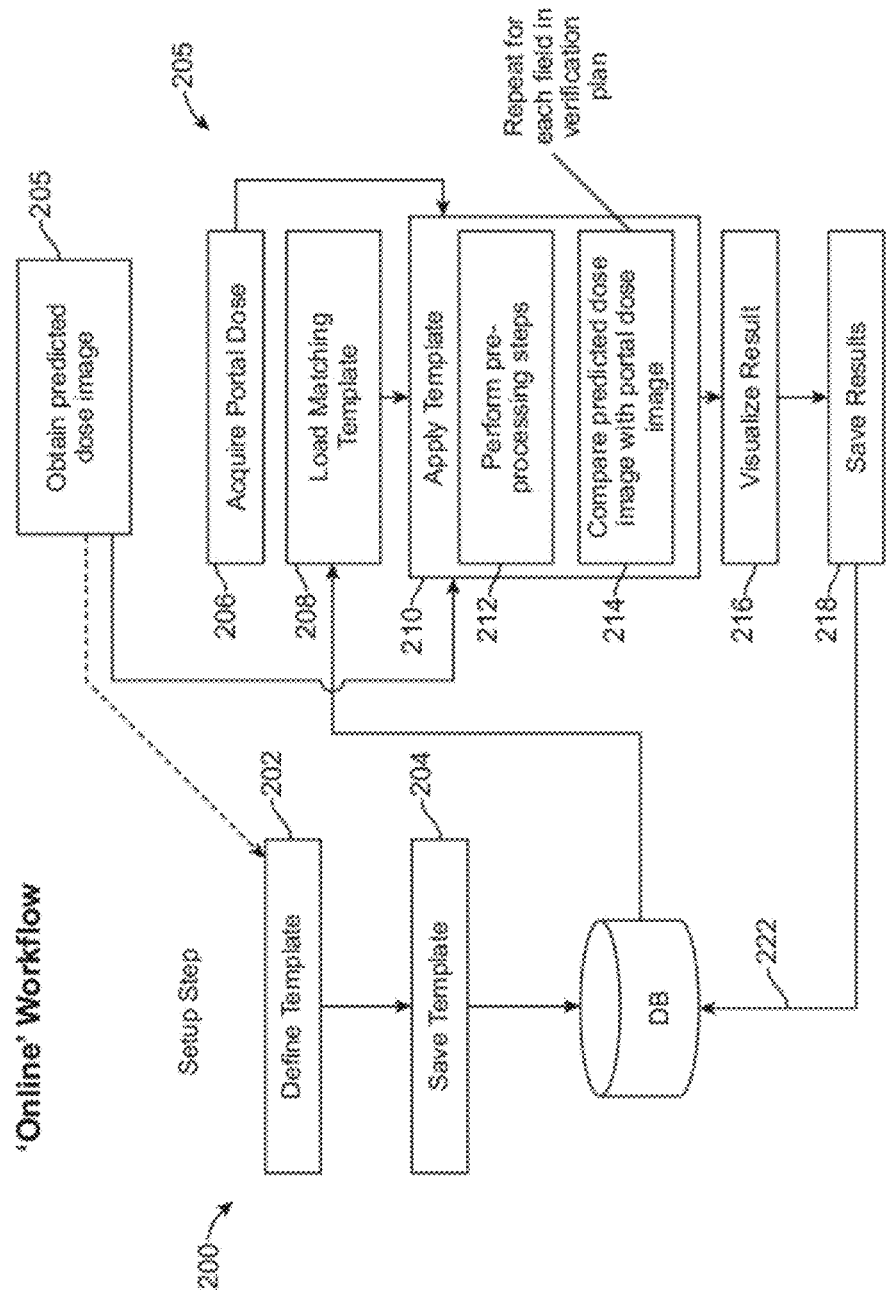
FIG. 2 illustrates a process for creating a template for dose evaluation, and a process for evaluating portal dose image(s) in accordance with some embodiments.

FIG. 2 illustrates a process 200 for creating a template for evaluating portal image(s) in accordance with some embodiments. As used in this specification, the term "image" is not limited to image that is displayed, and may include image data that is not displayed. In some embodiments, the creation of the template(s) may be done as a setup step (e.g., during a preparation for quality assurance testing, a patient setup, or a machine setup process that occurs before a treatment session). In other embodiments, the creation of the template(s) may be done any time before a treatment session begins. Also, in further embodiments, the creation of the template(s) may be done during a treatment session (e.g., between deliveries of radiation beams) or after a treatment session (e.g., for treatment verification). In such cases, the template-based method described herein may be used for analyzing actual dose image—dose image acquired with the patient on the support.

Figure 3:
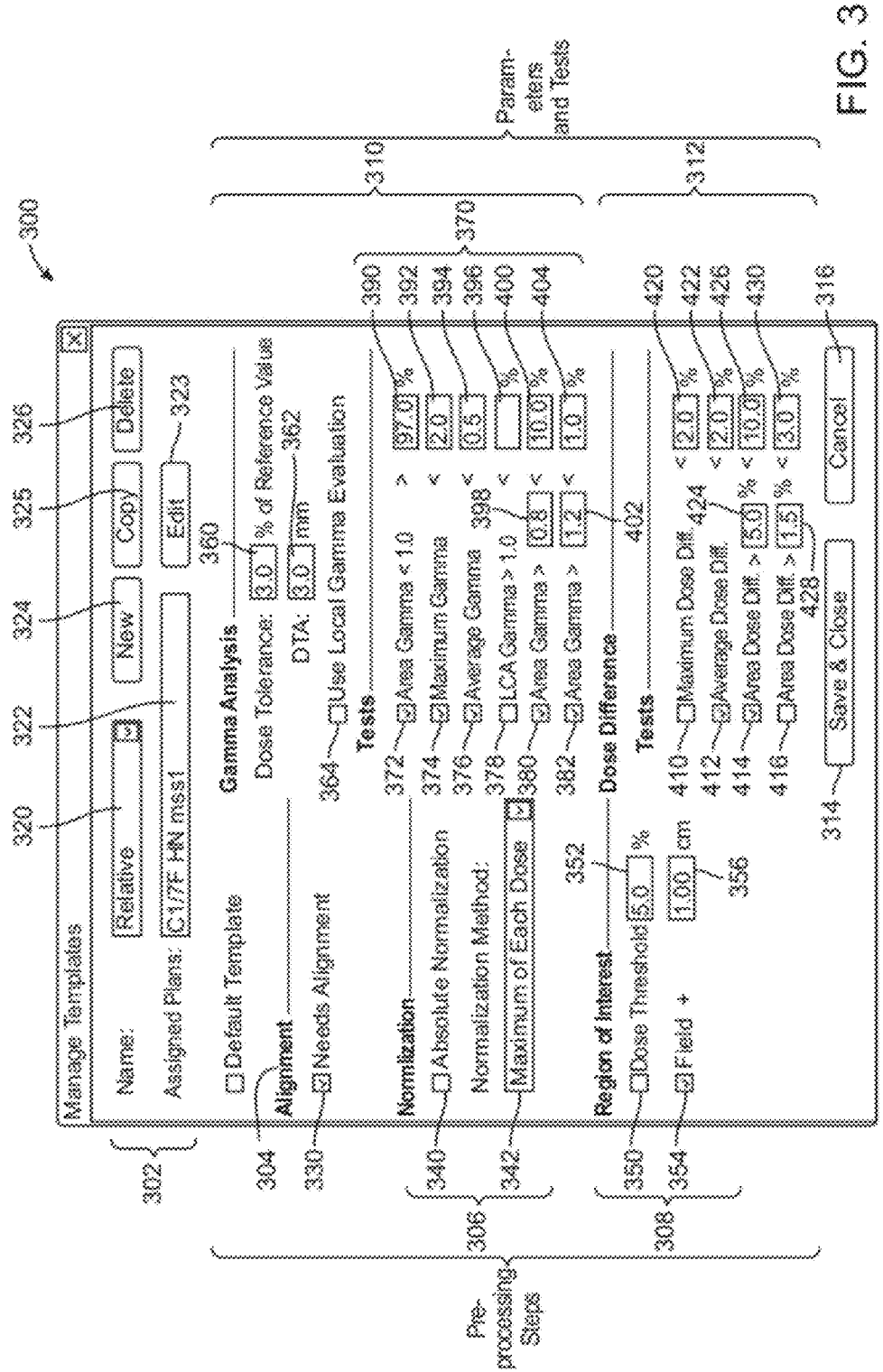
FIG. 3 illustrates a user interface for allowing a user to define a template for use in evaluating portal dose image(s) in accordance with some embodiments.

First a template for dose evaluation is defined (step 202). In the illustrated embodiments, a user interface may be provided in a screen (e.g., a computer screen, or a PDA screen) that allows a user to define the template. FIG. 3 illustrates an example of a user interface 300 for defining a template in accordance with some embodiments. The user interface 300 may be displayed on a screen in response to a processor (e.g., a processor in a computer at a user station, or the processor 54 of FIG. 1) executing a set of instructions. In some embodiments, the instructions may be stored in a computer system, such as a laptop or a desktop, or a device memory, for use by the user. In other embodiments, the instructions may be stored in a database for web-based application. In such cases, the user may log into a website or an intranet to access the user interface for defining the template. In some embodiments, the user interface may be configured to request for a user identification and a user password. In such cases, the processor will allow the user who has user right to access existing template(s) and/or to create new template(s).

It should be noted that as used in this specification, the term "processor" (such as the processor that is being described for performing various functions herein) is not limited to the processor 54 of FIG. 1, and may refer to any processing device that is specifically configured (e.g., programmed and/or built) to perform the various functions described herein, wherein such processing device may include one or more processing modules.

As shown in the figure, the user interface 300 includes a setup section 302, an alignment field 304, a normalization section 306, a region of interest section 308, a gamma analysis section 310, and a dose difference section 312.

The setup section 302 includes a field 320 for setup identification, and a field 322 for identifying assigned plan(s). The user may define multiple templates. The Setup ID corresponding to field 320 allows the user to give a unique name to the template, which distinguishes it from other templates. The plan(s) that is identified in the field 322 is associated with the template being created/edited. In some embodiments, a plan may include one or more treatment sessions, wherein each treatment session may include one or more radiation treatment fields. The setup section 302 also includes an "edit" button 323 for allowing a user to identify the plan(s) that is associated with the template. The setup section 302 also includes a "new" button 324 for allowing a user to create a new template, a "copy" button 325 for allowing a user to copy data from the current template to a new template, and a "delete" button 326 for allowing a user to delete a template.

The alignment field 304 includes a checkbox 330. When the alignment checkbox 330 is checked by the user, the template prescribes an alignment to be performed so that the predicted dose image(s) is aligned with the respective portal dose image(s), e.g., to correct for geometric errors. An example of such geometric error is the error in positioning of the imager 100.

The normalization section 306 of the user interface 300 allows a user to select between two types of image normalization: absolute normalization and relative normalization. In particular, when the absolute normalization box 340 is checked, the template prescribes absolute normalization to be performed, which preserves the full absolute dose information (i.e., the dose information that is acquired with the portal dose image, wherein dose data is not rescaled to some artificial normalization point) in the portal dose image. On the other hand, when the absolute normalization box 340 is not checked, then the template will prescribe relative normalization to be performed during the dose evaluation process. The relative normalization allows a user to rescale the portal dose image(s) and the predicted dose image(s) to some selected normalization points for a specific study. The selection for the normalization point may be (1) maximum of predicted dose, (2) maximum of each dose, (3) selected point in dose, or (4) dose in isocenter. As shown in the figure, the normalization section 306 includes a pull-down menu 342, which when selected, will provide these four options for normalization point to be selected. If "maximum of predicted dose" is selected, each point in the portal dose image(s) will be divided by the maximum value of the predicted dose for the field under study, thereby normalizing the values in the portal dose image(s) with respect to the maximum value of the predicted dose. The predicted dose image(s) will be normalized in a similar manner. If "maximum of each dose" is selected, each point in the portal dose image will be divided by the maximum value in the corresponding portal dose image, thereby normalizing the values in the portal dose image with respect to the respective maximum value in the portal dose image. Also the predicted dose image is normalized with respect to the maximum value in the predicted dose image. If "selected point in dose" is selected, each point in the portal dose image(s) will be divided by the dose value at a user-selected point, thereby normalizing the values in the portal dose image(s) with respect to the dose value at the user-selected point. The same also applies to the predicted dose image, wherein a point is chosen, and the image is normalized to the dose at that point. If "dose in isocenter" is selected, each point in the portal dose image(s) will be divided by the dose value at the isocenter, thereby normalizing the values in the portal dose image(s) with respect to the dose value at the isocenter. The same also applies to the predicted dose image.

The region of interest section 308 allows the user to prescribe the dose evaluation analysis to be performed on a particular portion of the portal dose image. The region of interest section 308 includes a dose threshold box 350 with a corresponding input field 352, and a "field +" box 354 with a corresponding input field 356. When the dose threshold box 350 is checked, it allows the user to enter a dose threshold value (e.g., in unit of percentage) in the corresponding input field 352. The dose threshold value sets a filter level to filter out low dose values, such as values that are resulted from noise or transmission. When the field box 354 is checked, it allows the user to enter a margin value (e.g., in unit of cm) in the corresponding input field 356, which defines a margin around the field defined by the collimator. In other embodiments, the user interface may allow the user to draw an outline on a graph to thereby define the region of interest. In some cases, the outline (ROI box) may be drawn directly on a blend (or overlay) of the portal dose image and the predicted dose image.

The gamma analysis section 310 includes a dose tolerance field 360, a distance to agreement (DTA) field 362, and a checkbox 364 for local gamma evaluation. The dose tolerance field 360 allows a user to enter a value to set the dose tolerance (e.g., in unit of percentage) in relation to a reference value. If "local gamma evaluation" is not selected, such reference value is the maximum value in the field after omitting certain high "outlier" values that are determined by a user preference. When "local gamma evaluation" is selected, this reference value is a planned dose at the point (pixel) under evaluation. The DTA field 362 allows a user to set the DTA (e.g., in unit of mm). When the checkbox 364 for local gamma evaluation is checked by the user, the template prescribes the dose evaluation to use local gamma evaluation. In the local gamma evaluation, a local dose reference value (instead of a global dose reference value— e.g., a maximum of predicted dose) is used. The local dose reference value may be a local value of the predicted dose at the pixel being evaluated. When the checkbox 364 is not checked, the template prescribes the dose evaluation to use global gamma evaluation technique in which a global dose reference value is used.

In some embodiments, when performing gamma analysis, the processor compares a portal dose image with a predicted dose image. The gamma analysis uses a metric (or quality index) to measure the similarity (or difference) between the two images, wherein such metric represents a measure of the dose difference and the DTA. The dose difference is the difference in value between the calculated and measured doses. The DTA is the distance between a measured dose point and the nearest point in the calculated distribution with the same dose value. Thus, in some embodiments, the gamma values may be used to show the difference between the calculated and measured doses relative to acceptance tolerances (e.g., dose difference threshold, DTA threshold). The gamma index represents disagreement in the regions that fail the acceptance criteria and indicates quality in the regions that pass.

The gamma analysis section 310 also includes a tests section 370 for allowing the user to set different parameters for the gamma analysis. The tests section 370 includes checkboxes 372-382 for (1) "Area Gamma <1.0" test, (2)

"Maximum Gamma" test, (3) "Average Gamma" test, (4) "LCA gamma >1.0" test, (5) first user-defined "Area Gamma" test, and (6) second user-defined "Area Gamma" test, respectively. Each of these tests is described in more detail below.

When the checkbox 372 for the "Area Gamma <1.0" test is checked by the user, it prescribes such test to be performed in the dose image analysis. The user may enter a value in the corresponding field 390 that sets the allowed area (e.g., in unit of percentage) of gamma with value less than 1. In the illustrated example of FIG. 3, the allowed area is set to be more than 97.0%. In such case, when the processor performs evaluation on the portal dose image, the processor will analyze the portal dose image with respect to the predicted dose image, and will determine if the area in the portal image with gamma value that is less than 1 is more than 97% of the total area (e.g., the treatment area, or the area of the region of interest) being evaluated. In some embodiments, if the area in the portal image with gamma value <1 is more than the value set in the field 390, the processor then automatically determines that the test for "Area Gamma <1.0" is passed. Otherwise, the processor automatically determines that the test is failed. It should be noted that in other embodiments, the value that may be inputted for the "Area Gamma <1.0" test may be different from the example illustrated.

When the checkbox 374 for the "Maximum Gamma" test is checked by the user, it prescribes such test to be performed in the dose image analysis. The user may enter a value in the corresponding field 392 that sets the allowed maximum gamma value. In the illustrated example of FIG. 3, the allowed maximum gamma value is set to be less than 2.0. In such case, when the processor performs evaluation on the portal dose image, the processor will analyze the portal dose image with respect to the predicted dose image to obtain gamma values, and will determine if the maximum gamma value is less than 2.0. In some embodiments, if the maximum calculated gamma value is less than the value set in the field 292, the processor then automatically determines that the test for "Maximum Gamma" is passed. Otherwise, the processor automatically determines that the test is failed. It should be noted that in other embodiments, the value that may be inputted for the "Maximum Gamma" test may be different from the example illustrated.

When the checkbox 376 for the "Average Gamma" test is checked by the user, it prescribes such test to be performed in the dose image analysis. The user may enter a value in the corresponding field 394 that sets the allowed average gamma value. In the illustrated example of FIG. 3, the allowed average gamma value is set to be less than 0.5. In such case, when the processor performs evaluation on the portal dose image, the processor will analyze the portal dose image with respect to the predicted dose image to obtain gamma values, and will determine if the average gamma value (in the treatment area or region of interest) is less than 0.5. In some embodiments, if the average gamma value is less than the value set in the field 394, the processor then automatically determines that the test for "Average Gamma" is passed. Otherwise the processor automatically determines that the test is failed. It should be noted that in other embodiments, the value that may be inputted for the "Average Gamma" test may be different from the example illustrated.

When the checkbox 378 for the "LCA Gamma >1.0" test is checked by the user, it prescribes such test to be performed in the dose image analysis. The user may enter a value in the corresponding field 396 to set the allowed largest connected area (LCA) (e.g., in unit of percentage) with gamma value that is greater than 1.0. For example, the allowed LCA may be set in field 396 to be 6%. In such case, when the processor performs evaluation on the portal dose image, the processor will analyze the portal dose image with respect to the predicted dose image to obtain gamma values, and will determine if the largest connected area in the image that has gamma value greater than 1.0 is less than 6% of the total area (e.g., area or number of pixels in the treatment area or region of interest). In some embodiments, if the LCA is less than the value set in the field 396, the processor then automatically determines that the test for "LCA Gamma >1.0" is passed. Otherwise the processor automatically determines that the test is failed. It should be noted that in other embodiments, the value that may be inputted for the "LCA Gamma >1.0" test may be different from the example illustrated.

When the checkbox 380 for the first user-defined "Area Gamma" test is checked by the user, it prescribes such test to be performed in the dose image analysis. The user may enter a value in field 398 that sets the threshold level for the gamma value, and a value in field 400 that sets the allowable area (e.g., in unit of percentage) that can exceed the gamma threshold level in field 398. In the illustrated example of FIG. 3, the gamma threshold level is set to be 0.8, and the allowable area is set to be 10%. In such case, when the processor performs evaluation on the portal dose image, the processor will analyze the portal dose image with respect to the predicted dose image to obtain gamma values, and will determine if the area with gamma value that is >0.8 is less than 10% (e.g., of the area being analyzed, such as the region of interest). In some embodiments, if the area with gamma value that is >0.8 is less than 10%, the processor then automatically determines that the test for the first user-defined "Area Gamma" test is passed. Otherwise the processor automatically determines that the test is failed. It should be noted that in other embodiments, the values that may be inputted for the first user-defined "Area Gamma" test may be different from the examples illustrated.

When the checkbox 382 for the second user-defined "Area Gamma" test is checked by the user, it prescribes such test to be performed in the dose image analysis. The user may enter a value in field 402 that sets the threshold level for the gamma value, and a value in field 404 that sets the allowable area (e.g., in unit of percentage) that can exceed the gamma threshold level in field 402. In the illustrated example of FIG. 3, the gamma threshold level is set to be 1.2, and the allowable area is set to be 1.0%. In such case, when the processor performs evaluation on the portal dose image, the processor will analyze the portal dose image with respect to the predicted dose image to obtain gamma values, and will determine if the area with gamma value that is >1.2 is less than 1% (e.g., of the area being analyzed, such as the region of interest). In some embodiments, if the area with gamma value that is >1.2 is less than 1%, the processor then automatically determines that the test for the second user-defined "Area Gamma" test is passed. Otherwise the processor automatically determines that the test is failed. It should be noted that in other embodiments, the values that may be inputted for the second user-defined "Area Gamma" test may be different from the examples illustrated.

Although the example of the template shows two user-defined "Area Gamma" tests, in other embodiments, the template may include only one such user-defined Area Gamma test. Also, in other embodiments, the template may include more than two user-defined Area Gamma tests. For example, in some embodiments, the user interface may allow the user to enter as many user-defined Area Gamma tests as the user desires. The different Area Gamma tests allow dose image(s) to be analyzed using a same type of technique but different parameters and/or threshold values.

Returning to the user interface in FIG. 3, the dose difference test section 312 is for allowing the user to set different parameters and tests for the dose difference analysis. The dose difference test section 312 includes checkboxes 410-416 for (1) "Maximum Dose Difference" test, (2) "Average Dose Difference" test, (3) first user-defined "Area Dose Difference" test, and (4) second user-defined "Area Dose Difference test." Each of these tests is described in more detail below.

When the checkbox 410 for the "Maximum Dose Difference" test is checked by the user, it prescribes such test to be performed in the dose image analysis. The user may enter a value in the corresponding field 420 that sets the allowed maximum dose difference (e.g., in unit of percentage in which the image values are in "relative" normalization, or in calibration unit (CU) in which the image values are in "absolute" normalization). For example, the allowed maximum dose difference may be set to be less than 2.0%. In such case, when the processor performs evaluation on the portal dose image, the processor will analyze the portal dose image with respect to the predicted dose image to calculate dose difference values, and will determine if the maximum dose difference value is less than 2.0%. In some embodiments, the dose difference value is determined on a pixel-by-pixel basis—e.g., for each pixel: dose difference value=(measured dose value−predicted dose value). In some embodiments, the measured dose value, the predicted does value, and the dose difference value have "%" as units. In other embodiments, the measured dose value, the predicted does value, and the dose difference value are in calibration units. In some embodiments, if the maximum dose difference value is less than the value set in the field 420 (which is 2.0% in the example), the processor then automatically determines that the test for "Maximum Dose Difference" is passed. Otherwise, the processor automatically determines that the test is failed. It should be noted that in other embodiments, the value that may be inputted for the "Maximum Dose Difference" test may be different from the example illustrated.

When the checkbox 412 for the "Average Dose Difference" test is checked by the user, it prescribes such test to be performed in the dose image analysis. The user may enter a value in the corresponding field 422 that sets the allowed average dose difference (e.g., in unit of percentage or calibration unit). In the illustrated example of FIG. 3, the allowed average dose difference is set to be less than 2.0%. In such case, when the processor performs evaluation on the portal dose image, the processor will analyze the portal dose image with respect to the predicted dose image to determine dose difference values (for all of the pixels within the defined region of interest), determine an average of the determined dose difference values, and will determine if the average dose difference value is less than 2.0%. In some embodiments, if the average dose difference value is less than the value set in the field 422 (which is 2.0% in the example), the processor then automatically determines that the test for "Average Dose Difference" is passed. Otherwise, the processor automatically determines that the test is failed. It should be noted that in other embodiments, the value that may be inputted for the "Average Dose Difference" test may be different from the example illustrated.

When the checkbox 414 for the first user-defined "Area Dose Difference" test is checked by the user, it prescribes such test to be performed in the dose image analysis. The user may enter a value in field 424 that sets the threshold level for the area dose difference value, and a value in field 426 that sets the allowable area (e.g., in unit of percentage) that can exceed the area dose difference threshold level in field 424. In the illustrated example of FIG. 3, the area dose difference threshold level is set to be 5.0, and the allowable area is set to be 10%. In such case, when the processor performs evaluation on the portal dose image, the processor will analyze the portal dose image with respect to the predicted dose image to obtain dose difference values for all pixels of the area being analyzed, and will determine if the combined area with dose difference value that is >5.0 is less than 10% (e.g., of the total area being analyzed, such as the region of interest). For example, the processor may determine dose difference on a pixel-by-pixel basis for the region of interest, count up all pixels that are greater than threshold, then express that count of pixels as a percentage of all pixels in the region of interest. In some embodiments, if the area with dose difference value that is >5.0 is less than 10% of the total area being analyzed, the processor then automatically determines that the test for the first user-defined "Area Dose Difference" test is passed. Otherwise the processor automatically determines that the test is failed. It should be noted that in other embodiments, the values that may be inputted for the first user-defined "Area Dose Difference" test may be different from the examples illustrated.

When the checkbox 416 for the second user-defined "Area Dose Difference" test is checked by the user, it prescribes such test to be performed in the dose image analysis. The user may enter a value in field 428 that sets the threshold level for the area dose difference value, and a value in field 430 that sets the allowable area (e.g., in unit of percentage) that can exceed the area dose difference level in field 428. In the illustrated example of FIG. 3, the area dose difference level is set to be 1.5, and the allowable area is set to be 3.0%. In such case, when the processor performs evaluation on the portal dose image, the processor will analyze the portal dose image with respect to the predicted dose image to obtain dose difference values for all pixels of the area being analyzed, and will determine if the combined area with dose difference value that is >1.5 is less than 3% (e.g., of the area being analyzed, such as the region of interest). In some embodiments, if the area with dose difference value that is >1.5 is less than 3% of the total area being analyzed, the processor then automatically determines that the test for the second user-defined "Area Dose Difference" test is passed. Otherwise the processor automatically determines that the test is failed. It should be noted that in other embodiments, the values that may be inputted for the second user-defined "Area Dose Difference" test may be different from the examples illustrated.

Although the example of the template shows two user-defined "Area Dose Difference" tests, in other embodiments, the template may include only one such user-defined Area Dose Difference test. Also, in other embodiments, the template may include no user-defined Area Dose Difference test, or more than two user-defined Area Dose Difference tests. For example, in some embodiments, the user interface may allow the user to enter as many user-defined Area Dose Difference tests as the user desires. The different Area Dose Difference tests allow dose image(s) to be analyzed using a same type of technique but different parameters and/or threshold values.

As shown in FIG. 3, the user interface 300 also includes a "Save and Close" button 314 for allowing the user to save the input for the template, and a "Cancel" button 316 for allowing the user to cancel the template definition/editing operation.

Returning to FIG. 2, in the process 200, after the template is defined, the template is then saved in a medium, such as a database (Step 204). Such may be accomplished using the "Save and Close" button 314 in the user interface 300. In some embodiments, the template may be stored in the medium by saving the information that is inputted using the user interface 300. The stored template may be later used in a dose evaluation process. In some embodiments, the predicted dose image may be obtained (step 205), and is then associated with the template. For example, the predicted dose image may be stored as a part of the template, or alternatively, be stored in a location that can be accessed by the template.

In some embodiments, prior to a radiation treatment session, an IMRT plan is verified dosimetrically by creating a verification plan that contains fields with same geometry and shape as the treatment fields in the IMRT plan. The radiation machine 10 is then activated to deliver radiation in accordance with the verification plan (without the patient present, and with retracted couch), and the dose is recorded for each field using the portal imager 100 (e.g., the imager pixel intensity values are converted to dose based on a user calibration of the imager). The recorded dose images are then compared against respective predicted dose images. In some embodiments, several different tests may be performed to compare each pair of images (recorded dose image and the predicted dose image) to ensure that the recorded and predicted dose images are similar enough. A user, such as a medical physicist, then reviews the test results, and determines if the treatment plan is accepted or denied for treatment.

FIG. 2 shows an example of a dose evaluation process 205 in accordance with some embodiments. In some cases, the dose evaluation process 205 may include the template creation process 200. In the dose evaluation process 205, a portal dose image is first acquired (Step 206). Such may be accomplished using the system 10 of FIG. 1. For example, in some embodiments, the portal dose image may be for a certain field of an IMRT plan (e.g., an IMRT treatment plan or an IMRT verification plan). In such cases, the portal dose image is obtained by operating the collimator 22 in accordance with a treatment plan, activating the radiation source 20, and obtaining the image using the imager 100. The operation of the collimator 22 and the radiation source 20 is performed for an IMRT field according to the IMRT plan, and the resulting radiation received by the imager 100 will have different intensity at different regions in the image. The dose image from the imager 100 is then transmitted to the processor (such as the processor 54 in FIG. 1) for processing. Thus, in some embodiments, the template-based dose evaluation may be performed online in which the processor performs the dose evaluation during an operation of the radiation machine 10, or while the radiation machine 10 is "on" or is in a stand-by mode in which the machine 10 is ready to deliver additional radiation. In other embodiments, the template-based dose evaluation may be performed offline. In such cases, the portal dose images are obtained first, and are saved in a medium (e.g., in a database) for later processing. In such cases, the act of acquiring the portal dose image (Step 206) may be performed by the processor 54 receiving (e.g., retrieving, uploading, etc.) a previously stored portal dose image(s) from a medium (e.g., after a session for operating the machine 10 is over).

Next, the stored template is retrieved from the memory (Step 208). The memory may be any medium that is capable of storing data, and may be a database in some embodiments. In the illustrated embodiments, a plurality of templates that are previously created may be stored in a medium. In such cases, the act of obtaining the template may be accomplished by selecting one of the stored templates in the medium. In some cases, a user interface may be provided to a user for allowing the user to select a template from a list of previously created templates. Such user interface may also include functionalities, such as "open file," "close file," "save file," or "save file as," for allowing the user to manage files for the templates. In some embodiments, the act of obtaining the template from the memory may be performed by a processor. For example, the processor may process the user's request (which may include a path for a template file) to retrieve a template from a database, in which case, the processor will access the database that contains the template in order to obtain the template. In other embodiments, the retrieval of the template may be done automatically by the processor. For example, if a template has been previously associated with the plan, the processor may be configured to automatically retrieve the template based on the association with the plan.

Next, in the dose evaluation method 205, the processor applies the obtained template to the portal dose image and the predicted dose image to thereby perform the dose evaluation (Step 210). When performing the template-based dose evaluation, the processor uses the evaluation criteria (e.g., the pre-processing step(s), pre-processing parameter(s), the dose evaluation test(s), the parameter(s) associated with the dose evaluation test(s), the threshold(s) associated with the dose evaluation test(s), assigned plan(s), and/or any other information from the template) prescribed by the template. In particular, the processor first performs the pre-processing steps based on the information provided in the alignment section 304, the normalization section 306, and region of interest section 308 of the obtained template (Step 212). For example, if the box 330 for the alignment is checked in the template, the processor then automatically align the portal dose image with the predicted dose image. Also, the processor is configured (e.g., programmed, built, etc.) to automatically perform an absolute normalization on the portal dose image if the box 340 is checked. If the box 340 in the template is not checked, the processor is then configured to automatically perform a relative normalization on the portal dose image based on one of the normalization method selected in the pull-down menu 342. In addition, if a dose threshold 352 is provided in the region of interest section 308, the processor will then automatically filter out low dose values based on the dose threshold value. For example if the dose threshold value is set to 5%, then the processor will automatically filter out all dose values that are less than 5% of the maximum dose value. Also, if a margin 356 for a field is provided in the region of interest section 308 of the selected template, the processor will then automatically define a margin around the field defined by the jaws of the collimator. For example, if the margin value 356 is set to 1 cm, then the processor will automatically define a margin that is 1 cm outside and around the field defined by the jaws of the collimator.

After the pre-processing step(s) is performed in Step 212, the processor then performs dose evaluation on the portal dose image (Step 214). In particular, the processor will analyze the portal dose image with respect to predicted dose that is associated with the assigned plans (i.e., those listed in the field 322) associated with the template, wherein the predicted dose may be represented by a dose image. In the illustrated embodiments, the processor is configured to automatically perform gamma analysis and dose difference analysis using the parameters and tests specified in the gamma analysis section 310 and the dose difference section 312 of the selected template. For the gamma analysis, the processor will automatically perform the tests that have been selected by the user using the checkboxes 372-382. In the example shown in FIG. 3, boxes 372, 374, 376, 380, and 382 are checked, but not box 378. Thus, when the template is used by the processor to evaluate the portal dose image, the processor will automatically apply all of the tests that correspond with boxes 372, 374, 376, 380, and 382, but not the test for "LCA Gamma >1.0" in the illustrated example (because its corresponding box 378 is not checked in the template). Alternatively, the processor will automatically perform analysis on the dose image(s) using all of the different gamma tests regardless of whether the boxes 372-382 are checked on not. In such cases, the results of the analysis for the different tests will be presented to the user, but will not be used by the processor to determine a pass/fail status for the evaluation. In some embodiments, when performing the gamma analysis tests, the processor may be configured to calculate gamma values based on the criteria set forth in the fields 360, 362 once. Then the gamma values are processed in accordance with different analysis techniques prescribed by the different gamma analysis tests.

Similarly, for the dose difference analysis, the processor will automatically apply all of the tests that correspond to the user selections of checkboxes 410, 412, 416. In the illustrated example, the processor will automatically apply the tests that correspond with boxes 412 and 416, but not the test for "Maximum Dose Difference" and the second user-defined "Area Dose Difference" test (because the corresponding boxes 410, 416 for these two tests are not checked in the template). Alternatively, the processor will automatically perform analysis on the dose image(s) using all of the different dose difference tests regardless of whether the boxes 410-416 are checked on not. In such cases, the results of the analysis for the different tests will be presented to the user, but will not be used by the processor to determine a pass/fail status for the evaluation.

In some embodiments, the application of the template may be fully automatic in which the user selects a template to be applied to an entire session of images. In such cases, the template is retrieved from the database and is automatically applied to all portal dose images for that session. Such technique results in the same template being applied to all images. In other embodiments, the user may select a template to be applied to a particular portal dose image, and may then repeat that process for all other images. In such cases, the user has the option to apply different templates for different images.

In some embodiments, the template may be obtained first, and the step 210 is automatically repeated by the processor for processing the additional dose image(s), such as, dose images (e.g., portal dose images) acquired in a particular imaging session. In this configuration, the processor is only required to load the template (Step 208) once. The obtained template is then applied automatically by the processor to the plurality of dose images for dose evaluation. In some embodiments, the plurality of dose images may be a series of dose images that are acquired for a specific field or for a plurality of respective fields. It is possible to acquire multiple portal dose images for a specific field. Also, in some embodiments, the plurality of dose images may be obtained for different respective gantry angles of the system 10. In further embodiments, the dose images may be for different respective treatment sessions, or for different respective treatment plans. In some embodiments, if the assigned plan in the template includes a plurality of treatment radiation fields, then when the processor applies the template to evaluate the dose images that correspond to the assigned treatment plan, the processor will automatically apply the template to the plurality of dose images that correspond with the different treatment fields In some cases, instead of applying the template to multiple fields, the user may prescribe the processor (by using the user interface 300) to apply the template to only a single field in the treatment plan that includes multiple fields. Also, in some embodiments, the template may have a plurality of assigned plans, which may be for the same patient, or for different patients. In such cases, when the processor applies the template to evaluate dose image(s) in the assigned plans, the processor will automatically perform dose evaluation using the criteria set forth in the template for the plurality of treatment plans.

Figure 4:
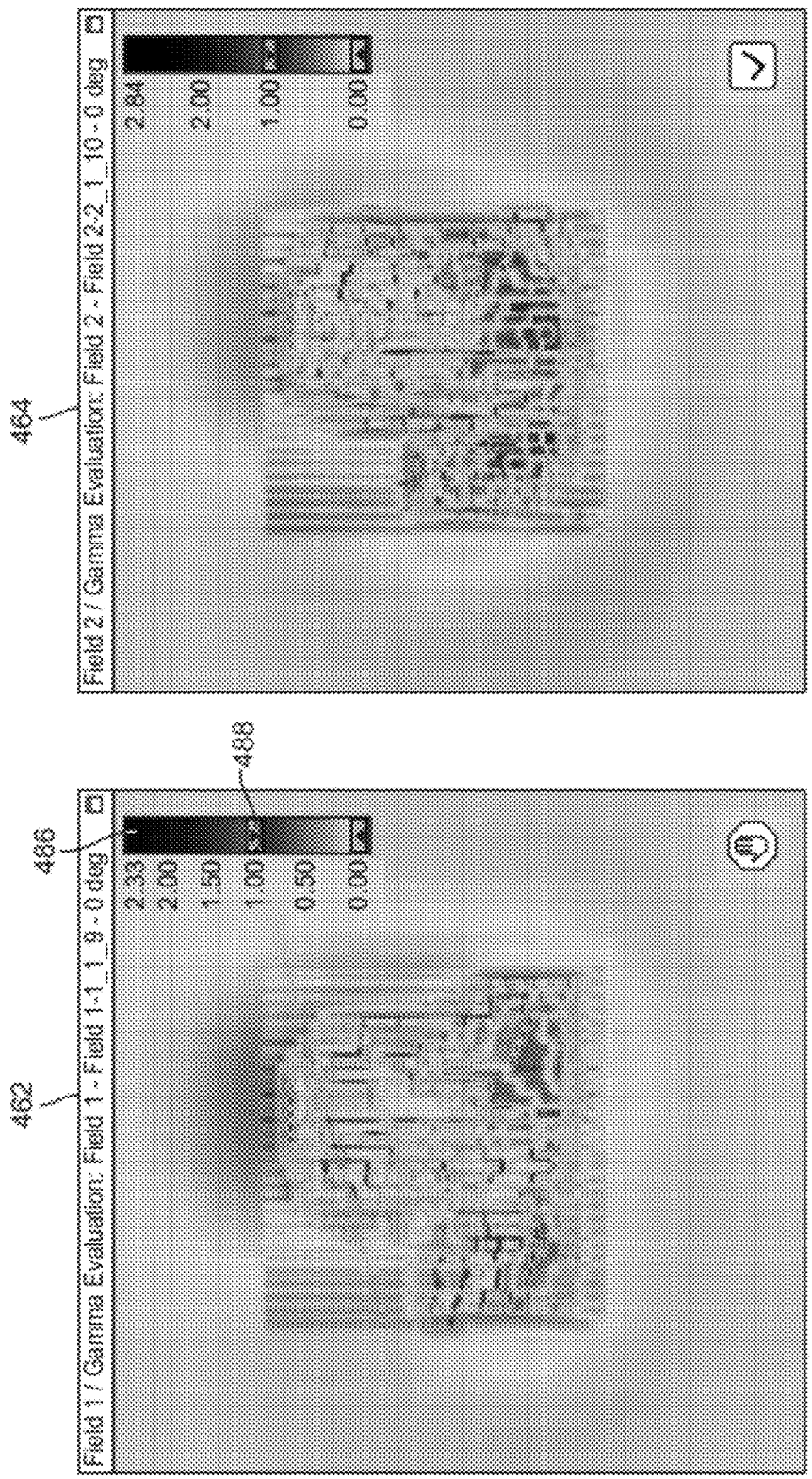
FIG. 4 illustrates an example of a result of a portal dose image evaluation, particularly showing gamma evaluation images.

Next, the result from the template based portal dose evaluation is presented to the user (Step 216). In some embodiments, a summary screen may be displayed to the user. The summary screen may present one or more graphs that summarize results of the gamma analysis. In some cases, a user may optionally choose to display in the summary, for all fields, dose difference or a blend (overlay) of portal and predicted doses. FIG. 4 illustrates six gamma evaluation graphs 462, 464, 466, 468, 470, 472 that illustrate results of the gamma analysis for six different fields, respectively. The graphs actually correspond to different respective gantry angles, despite the fact that each of the graphs shows that the gantry angle is at 0 degree. This is because a user may choose to perform the acquisition of portal dose images for different fields (that correspond to different respective gantry angles) at a single gantry angle (e.g., at 0 degree), thereby eliminating the tedious process of retracting the imager, moving to the new gantry angle, and then extending the imager again for each field. In the illustrated examples, each gamma graph includes a plurality of gamma values. Each gamma value is calculated for every pixel in the portal dose image, and represents the agreement of the portal dose image with the predicted image at that point. The gamma formalism results in a gamma "index" value for each point, wherein points with values of 1.0 or less represent a passing of the user's criteria of dose difference and distance to agreement (DTA) at the respective points, and values greater than 1.0 represents a failing of the criteria. In some embodiments, each gamma image may be colored based on the scale 486 in the upper right corner of the image. For example, the color light green may represent a value that is close to zero, wherein the scale may gradually increase to dark green representing a value that is close to 1.0. At 1.0, the color gradient may change to red (representing failure), and may increase from light red (for values above 1.0, but closer to 1.0) to dark red (for values above 1.0, but relatively further from 1.0). A slider 488 is provided on the scale bar 486 that allows the user to change the coloring of the image. For example, using the slider 488, a user may change both the bottom value and the green-to-red (or pass-to-fail) transition point. Note that this change by the slider 488 affects only the coloring of the image and does not affect the pass/fail numerical dose evaluation. Each gamma value in the gamma evaluation graph is a metric value that measures two variables—e.g., dose difference and DTA.

Figure 5A:
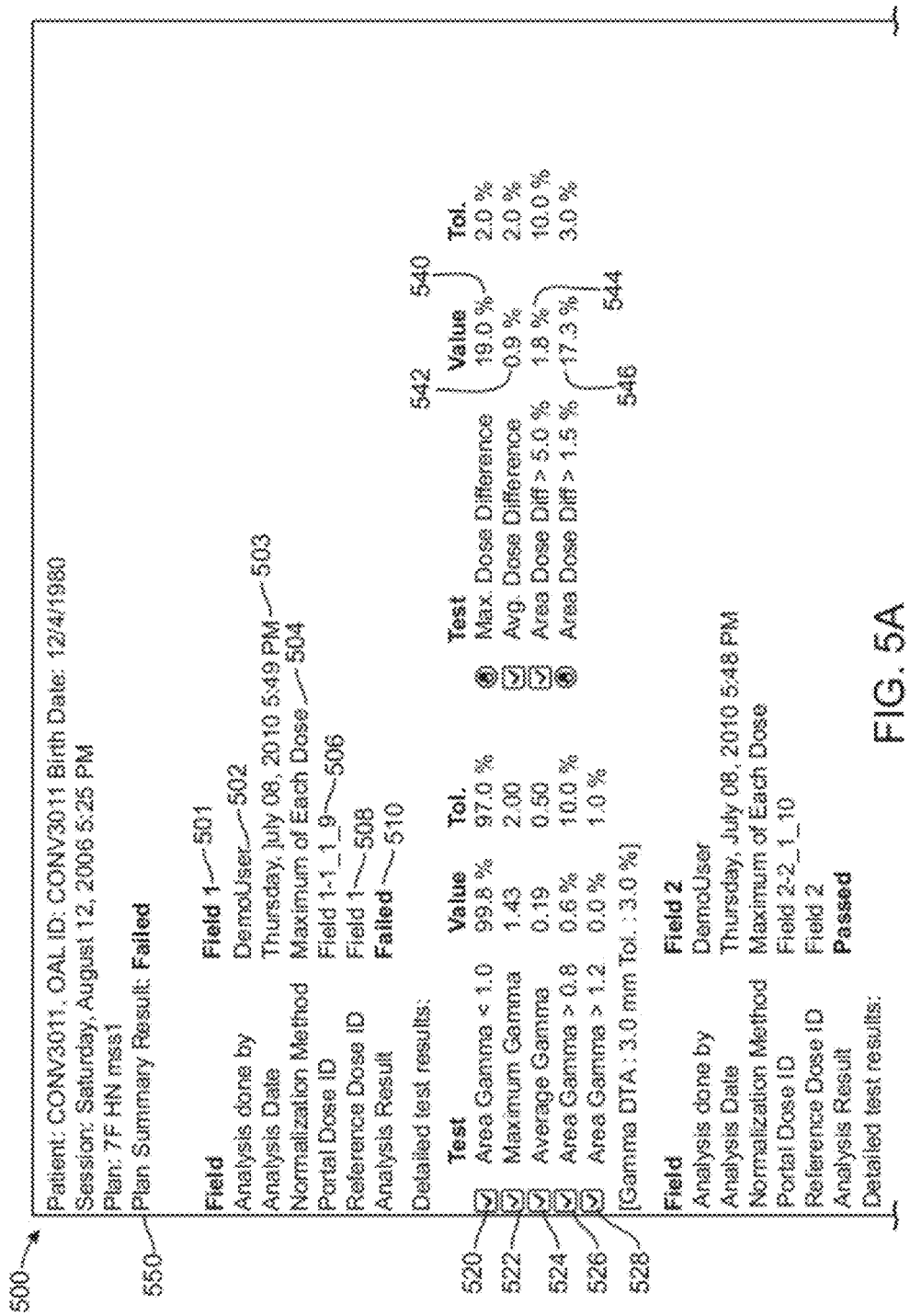
FIGS. 5A and 5B illustrate examples of reports that summarize results of a portal image evaluation.

Alternatively, or additionally, the summary screen may present the evaluation results in a table form to the user. For example, a report may be displayed on the screen that includes a textual summary of the performed tests, parameters and limits used in the tests, and the test results. FIG. 5A illustrates an example of a summary report 500 in accordance with some embodiments. The top of the summary report 500 includes information regarding the patient (e.g., patient identification, birth date, etc.), date and time of the analysis, and the plan (treatment plan/verification plan) identification. As shown in the example, the summary report 500 includes a treatment field identification 501, an identification 502 of the user who uses the template for the dose analysis, the date 503 on which the analysis is performed, the normalization method 504 used, the portal dose identification 506 (which is the identification of the portal dose image), and the reference dose identification 508 (which may be an identification of a predicted dose image associated with an assigned plan). The summary report 500 also includes an indicator 510 for indicating whether the dose evaluation passes all of the tests prescribed in the template for the assigned plan(s). In some embodiments, if one of the tests prescribed in the template fails, then the indicator 510 will indicate that the analysis "failed."

The summary report 500 also includes gamma analysis results 520-528, and dose difference analysis results 540-546. In the illustrated example, the gamma analysis result 520 shows that the area with gamma value that is less than 1.0 is 99.8%, when the tolerance is set to be at least 97% (which corresponds to the value input in field 390 of the template). Since the "Area Gamma <1.0" test is passed, a pass indicator (e.g., in the form of a check) is displayed next to the test. The gamma analysis result 522 shows that the maximum gamma value to be 1.43, when the maximum allowable is set by the template to be 2.0 (which corresponds to the value input in the field 392 of the template). Since the "Maximum Gamma" test is passed, a pass indicator (e.g., in the form of a check) is displayed next to the test. The gamma analysis result 524 shows that the average gamma value to be 0.19, when the maximum average gamma value is set to be 0.5 (which corresponds to the value input in field 394 of the template). Since the "Average Gamma" test is passed, a pass indicator (e.g., in the form of a check) is displayed next to the test. In accordance with the first user-defined "Area Gamma" test, the gamma analysis result 526 shows that 0.6% of the area being analyzed in the portal dose image has gamma value that is greater than 0.8 (which is the value prescribed by the input in field 398 of the template). Since the result of 0.6% is less than the allowable threshold of 10% as set forth in the field 400 of the template, the first user-defined "Area Gamma" test passes. Also, in accordance with the second user-defined "Area Gamma" test, the gamma analysis result 528 shows that none of the area being analyzed in the portal dose image has gamma value that is greater than 1.2 (which is the value prescribed by the input in field 402 of the template). Since the result of 0% is less than the allowable threshold of 1% as set forth in the field 404 of the template, the second user-defined "Area Gamma" test also passes in the illustrated example. In some embodiments, the report may further include additional indicators for indicating whether the first and second user-defined "Area Gamma" tests, respectively, pass or fail.

In the summary report 500, the dose difference analysis result 540 shows that the maximum dose difference between the obtained dose image and the predicted dose is 19%, when the allowable maximum is set to be 2.0% (which corresponds to the value input in the field 420 of the template). The dose difference analysis result 542 shows that the average dose difference is 0.9%, when the maximum allowable average dose difference is set to be 2.0% (which corresponds to the value input in the field 422 of the template). The dose difference analysis result 544 shows that 1.8% of the area being analyzed in the portal dose image has an area dose difference value that is greater than 10.0%. This means that 1.8% of the pixels within the evaluation area exceeds a difference of 10%. The dose difference analysis result 546 shows that 17.3% of the area being analyzed in the portal dose image has an area dose difference value that is greater than 3.0%.

In the illustrated example, the summary report 500 includes results of analysis for three different fields (Field 1, Field 2, Field 3) that are associated with the plan identified on top of the report 500. In other embodiments, the summary report 500 may include results of analysis for less than three different fields (e.g., for one field), or for more than three different fields. Also, as shown in the figure, the summary report 500 also includes a pass/fail indicator 550 for indicating whether the dose evaluation for the plan fails or passes. In some embodiments, the processor determines that the plan passes if all of the tests for all of the portal dose images for different fields pass. In such cases, if any of the tests for any of the portal dose images fails, then the processor determines that the plan fails.

Figure 5B:
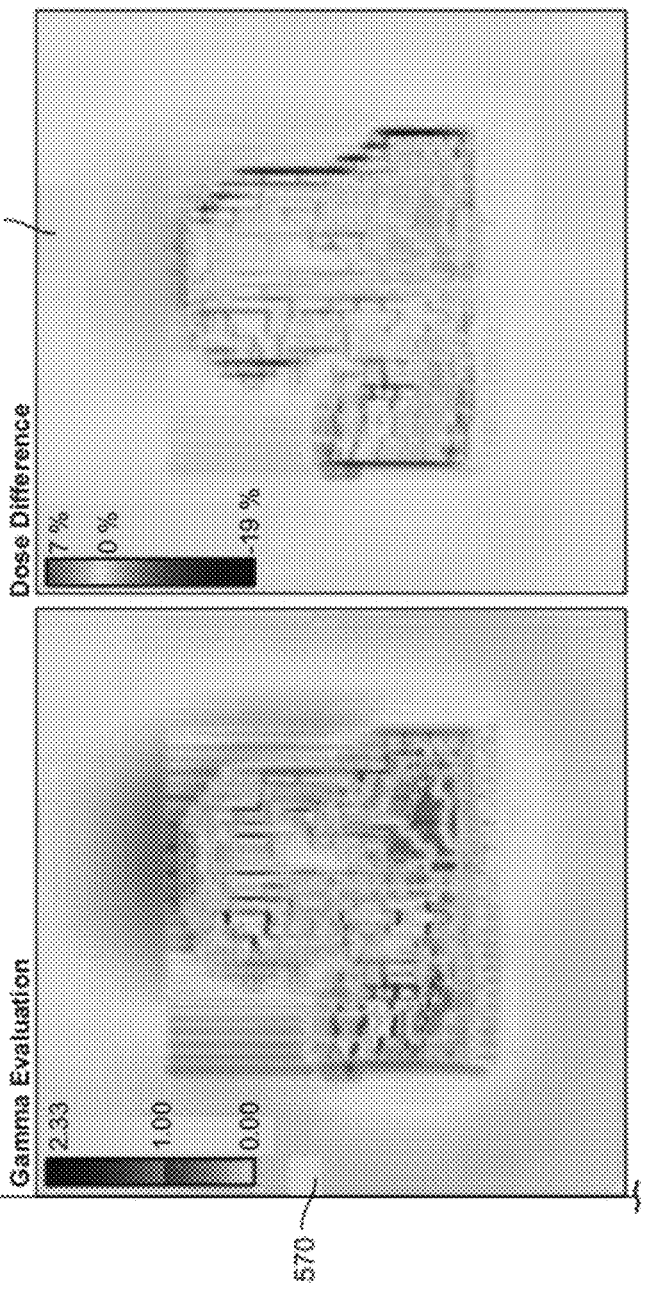
Figure 5B:
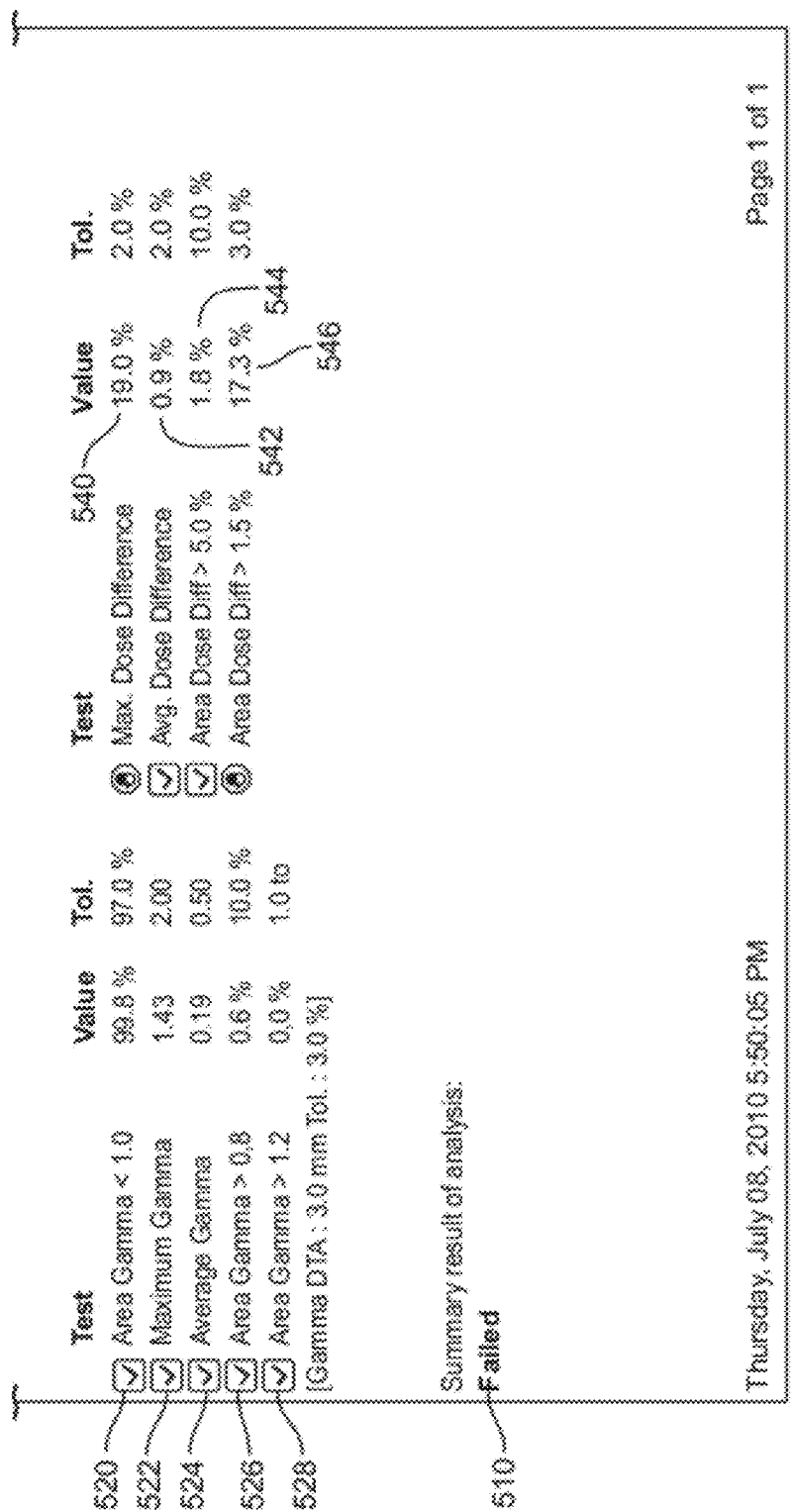

In other embodiments, the report may also include a graphical representation of the gamma and dose difference analysis. FIG. 5B illustrates another example of a summary report 562. The summary report 562 includes summary of the performed tests, parameters and limits used in the tests, and the test results for a specific field (e.g., "Field 1"). The summary report 562 also includes a graphical representation 570 of the gamma analysis, and a graphical representation 572 of the dose difference analysis for the specific field. As shown in the figure, a pass/fail indicator 510 is provided to inform the user whether the analysis failed or passed for the given field. In some embodiments, a report (like that shown in FIG. 5B) may be presented for each of the plurality of dose images. In such cases, the screen may display a plurality of such reports for the respective dose images (which may be for different fields, different sessions, or different plans).

In any of the embodiments described herein the analysis summary presented on the screen may be printed out by the processor. For example, in some embodiments, the user interface may include a print button for allowing a user to print the analysis summary.

As illustrated in the above embodiments, the template-based dose evaluation technique allows a user to efficiently obtain dose evaluation results. The template-based dose evaluation technique obviates the need for a user to manually perform repetitive work by defining the required steps, tests, parameters, and thresholds only once in a template. Then the same template may be applied by the processor to automatically perform dose evaluation for different dose images (e.g., portal dose images for different respective fields in a treatment plan, different dose images from different treatment plans for the same patient, or different dose images from different treatment plans for different patients). Such technique saves significant time and manual effort compared to having a user manually define parameters for each test, run each test using a processor, examining the test result for the test, and repeat the same steps manually for different parameters and for different tests.

Also, the embodiments of the dose evaluation technique described herein are advantageous because they provide a pass/fail indicator for each dose evaluation test for each dose image, thereby allowing a user to conveniently determine if any of the tests fails just by looking at the pass/fail indicator (e.g., without the need to compare result with the prescribed threshold). In addition, the embodiments of the dose evaluation technique described herein are also advantageous because they provide an overall pass/fail indicator for each dose image based on the results of the tests. This also allows the user to easily determine if the dose evaluation for a given dose image fails or passes without examining all of the test results. Furthermore, embodiments of the dose evaluation technique described herein are advantageous because the overall pass/fail indicator 550 for the plan allows the user to easily and quickly determine if the plan fails or not just by looking at the indicator 550. This obviates the need for the user to review each of the dose evaluation test results for each of the portal dose images in the plan.

As discussed, in some embodiments, the template-based dose evaluation may be performed offline. FIG. 6 illustrates an example of a user interface that allows a user to apply a dose evaluation template 600 to previously stored portal dose image(s) for evaluation against a predicted dose 606. In the example shown, four different templates (default template, test template, test absolute template, and test2 template) are available for the user to choose from. The portal dose image(s) may be for one or more fields (as provided in tab 602), or for one or more sessions (as provided in tab 604), wherein each session may include one or more fields for the treatment plan. After the dose evaluation is performed, the processor may display a summary 620, which summarizes the result of the dose evaluation for different portal dose images.

It should be noted that the template-based portal dose evaluation technique is not limited to the examples described previously, and that the template creation process 200 and the evaluation method 205 may have different variations in different embodiments. For example, in other embodiments, the template does not need to have all of the input fields shown in FIG. 3. Also, in other embodiments, the template may include other parameter(s), test(s), and/or pre-processing information that are different from those shown in FIG. 3. In addition, in other embodiments, instead of or in addition to providing input for gamma analysis and dose difference analysis, the template may include input for other types of analysis. The analysis may include any image processing, calculation, simulation, statistical analysis, or combination of the foregoing. Furthermore, in other embodiments, the template is not limited to being used for dose evaluation for IMRT, and may be used for other types of therapy, such as intensity modulated arc therapy (IMAT), or any treatment technique that involves use of radiation or charged particles (such as proton therapy). In other embodiments, the embodiments of the template approach described herein may be used for other processes that involve repetitive manual processing of data. For example, in other embodiments, the processor may apply a template to a collection of images for normalization, imager alignment, etc., which may or may not involve performing dose evaluation.

Computer System Architecture

Figure 7:
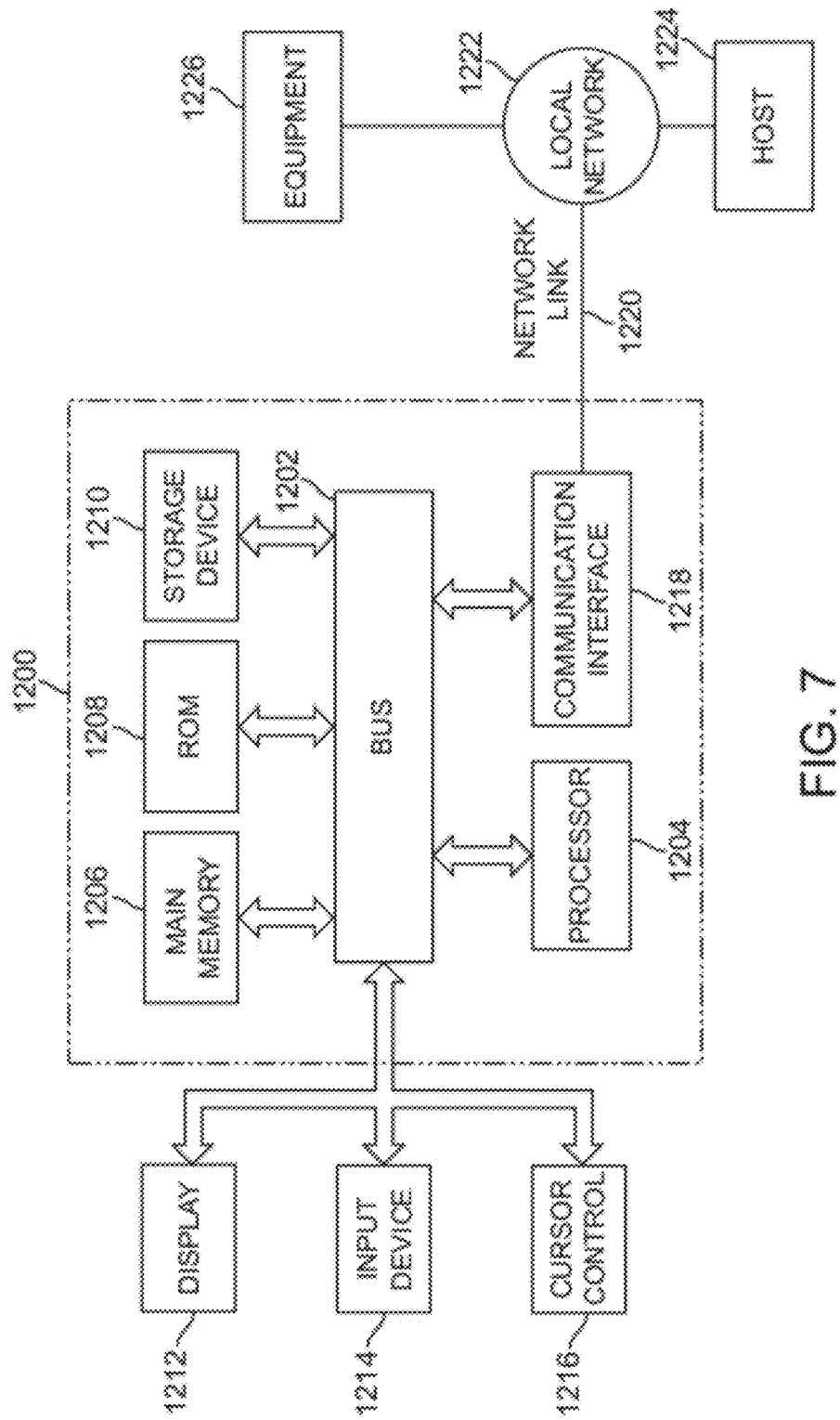
FIG. 7 is a block diagram of a computer system architecture, with which embodiments described herein may be implemented.

FIG. 7 is a block diagram that illustrates an embodiment of a computer system 1200 upon which an embodiment of the invention may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement functions of the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. Non-volatile medium may be considered to be an example of a non-transitory medium. Volatile media includes dynamic memory, such as the main memory 1206. Volatile medium may be considered to be another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of evaluating a portal dose image, comprising:
   obtaining a file of a template from a database, the template having one or more configurable field relating to dose image feature(s) to allow selectively prescribing of one or more evaluation parameters and one or more evaluation criteria, wherein the act of obtaining the template is performed by a processor;
   receiving a first portal dose image of a patient, wherein the first portal dose image is generated by a portal imager in response to radiation in accordance with a treatment plan, the treatment plan being different from the template; and
   after the first portal dose image is received, using the one or more evaluation parameters and the one or more evaluation criteria from the template by the processor to evaluate the first portal dose image.

2. The method of claim 1, further comprising automatically using the one or more evaluation criteria from the template to evaluate a second portal dose image.

3. The method of claim 2, wherein the first and second portal dose images are for different respective fields of the treatment plan.

4. The method of claim 2, wherein the first and second portal dose images are for different sessions of the treatment plan.

5. The method of claim 2, wherein the first portal dose image is for the treatment plan, and the second portal dose image is for another treatment plan.

6. The method of claim 1, wherein the one or more evaluation criteria comprises one or more tests, one or more thresholds, one or more tolerances, one or more preprocessing steps, or combination thereof.

7. The method of claim 1, wherein the database comprises a plurality of templates that include the template, and the act of obtaining the template comprises selecting the template from the plurality of templates.

8. The method of claim 1, wherein the act of evaluation is performed automatically after the first portal dose image is generated.

9. The method of claim 1, wherein the processor evaluates the first portal dose image by performing a first test and a second test, wherein the second test is automatically performed by the processor after the first test is performed.

10. The method of claim 1, further comprising using the processor to evaluate a second portal dose image, wherein the second portal dose image is evaluated automatically by the processor after the first portal dose image is evaluated.

11. The method of claim 1, further comprising:
    generating a report that summarizes a result of the evaluation; and
    storing the report in a medium or presenting the report on a screen.

12. The method of claim 11, wherein the report also summarizes another result of an evaluation of a second portal dose image.

13. The method of claim 12, wherein the report also provides an overall result that is derived from the results of the evaluations of the first and second portal dose images.

14. The method of claim 13, wherein the result of the evaluation of the first portal dose image comprises a first set of test results from a first plurality of tests for evaluating the first portal dose image, and the result of the evaluation of the second portal dose image comprises a second set of test results from a second plurality of tests for evaluating the second portal dose image.

15. The method of claim 1, further comprising:
    obtaining a first dose evaluation image using a first result of the evaluation; and
    displaying the first dose evaluation image on a screen.

16. The method of claim 15, further comprising:
obtaining a second dose evaluation image using a second result of an evaluation of a second portal dose image, wherein the act of obtaining the second dose evaluation image is performed automatically after the first dose evaluation image is obtained; and
displaying the second dose evaluation image on the screen.

17. The method of claim 1, wherein the first portal dose image is evaluated during an operation of a treatment radiation machine.

18. The method of claim 1, wherein the first portal dose image is evaluated while a treatment radiation machine is in a stand-by mode.

19. The method of claim 1, wherein the template prescribes multiple dose image tests be performed.

20. The method of claim 19, wherein the multiple dose image tests comprise (1) an area gamma test, (2) a maximum gamma test, (3) an average gamma test, (4) a gamma test with respect to a largest connected area (LCA), (5) a maximum dose difference value test, (6) an average dose difference value test, or (7) any combination of the foregoing.

21. The method of claim 1, wherein the template prescribes an area dose difference test be performed.

22. The method of claim 1, wherein the template prescribes multiple tests to be performed to evaluate the first portal dose image.

23. The method of claim 1, further comprising outputting multiple test results for the first portal dose image based on the template.

24. The method of claim 1, wherein the act of using the processor to evaluate the first portal dose image comprises using the processor to evaluate different aspects of the first portal dose image.

25. The method of claim 1, wherein the act of using the processor to evaluate the first portal dose image comprises determining if at least one of the one or more evaluation parameters satisfies at least one of the one or more evaluation criteria.

26. The method of claim 1, wherein the one or more evaluation parameters comprise multiple evaluation parameters, and the one or more evaluation criteria comprise multiple evaluation criteria for the respective multiple evaluation parameters; and
wherein the act of using the processor to evaluate the first portal dose image comprises determining if the multiple evaluation parameters satisfy the multiple evaluation criteria, respectively.

27. A system for evaluating a portal dose image, comprising:
a processor that is communicatively coupled to a database, the database having a file of a template that includes one or more configurable fields relating to dose image feature(s) to allow selectively prescribing of one or more evaluation parameters and one or more evaluation criteria;
wherein the processor is configured to (1) obtain the template from the database, (2) receive a first portal dose image of a patient, and (3) after the first portal dose image is received, use the one or more evaluation parameters and the one or more evaluation criteria from the template to evaluate the first portal dose image, wherein the first portal dose image is generated by a portal imager in response to radiation in accordance with a treatment plan, the treatment plan being different from the template.

28. The system of claim 27, wherein the processor is configured for automatically using the one or more evaluation criteria from the template to evaluate a second portal dose image.

29. The system of claim 28, wherein the first and second portal dose images are for different respective fields of the treatment plan.

30. The system of claim 28, wherein the first and second portal dose images are for different sessions of the treatment plan.

31. The system of claim 28, wherein the first portal dose image is for the treatment plan, and the second portal dose image is for another treatment plan.

32. The system of claim 27, wherein the one or more evaluation criteria comprises one or more tests, one or more thresholds, one or more tolerances, one or more preprocessing steps, or combination thereof.

33. The system of claim 27, further comprising a database that stores a plurality of templates, wherein the processor is configured to obtain the template by selecting the template from the plurality of templates.

34. The system of claim 27, wherein the processor is configured to perform the evaluation automatically after the first portal dose image is generated.

35. The system of claim 27, wherein the processor is configured to evaluate the first portal dose image by performing a first test and a second test, and wherein the processor is configured to automatically perform the second test after the first test is performed.

36. The system of claim 27, wherein the processor is configured to evaluate a second portal dose image automatically after the first portal dose image is evaluated.

37. The system of claim 27, wherein the processor is configured to generate a report that summarizes a result of the evaluation.

38. The system of claim 37, wherein the report also summarizes another result of an evaluation of a second portal dose image.

39. The system of claim 38, wherein the report also provides an overall result that is derived from the results of the evaluations of the first and second portal dose images.

40. The system of claim 39, wherein the result of the evaluation of the first portal dose image comprises a first set of test results from a first plurality of tests for evaluating the first portal dose image, and the result of the evaluation of the second portal dose image comprises a second set of test results from a second plurality of tests for evaluating the second portal dose image.

41. The system of claim 27, wherein the processor is configured to determine a first dose evaluation image using a first result of the evaluation, and automatically determine a second dose evaluation image after the first dose evaluation image is determined.

42. The system of claim 27, wherein the processor is configured to evaluate the first portal dose image during an operation of a treatment radiation machine.

43. The system of claim 27, wherein the processor is configured to evaluate the first portal dose image while a treatment radiation machine is in a stand-by mode.

44. The system of claim 27, wherein the template prescribes multiple dose image tests be performed.

45. The system of claim 44, wherein the multiple dose image tests comprise (1) an area gamma test, (2) a maximum gamma test, (3) an average gamma test, (4) a gamma test with respect to a largest connected area (LCA), (5) a maximum dose difference value test, (6) an average dose difference value test, or (7) any combination of the foregoing.

46. The system of claim 27, wherein the template prescribes an area dose difference test be performed.

47. The system of claim 27, wherein the template prescribes multiple tests to be performed to evaluate the first portal dose image.

48. The system of claim 27, wherein the processor is also configured to output multiple test results for the first portal dose image based on the template.

49. The system of claim 27, wherein the processor is configured to evaluate the first portal dose image by determining different aspects of the first portal dose image.

50. The system of claim 27, wherein the processor is configured to evaluate the first portal dose image by determining if at least one of the one or more evaluation parameters satisfies at least one of the one or more evaluation criteria.

51. The system of claim 27, wherein the one or more evaluation parameters comprise multiple evaluation parameters, and the one or more evaluation criteria comprise multiple evaluation criteria for the respective multiple evaluation parameters; and
wherein the processor is configured to evaluate the first portal dose image comprises by determining if the multiple evaluation parameters satisfy the multiple evaluation criteria, respectively.

52. A computer product having a non-transitory medium that stores a set of instruction, an execution of which by a processor causes a process for evaluating a portal dose image to be performed, the process comprising:
obtaining a file of a template from a database, the template having one or more configurable fields relating to dose image feature(s) to allow selectively prescribing of one or more evaluation parameters and one or more evaluation criteria;
receiving a first portal dose image of a patient, wherein the first portal dose image is generated by a portal imager in response to radiation in accordance with a treatment plan, the treatment plan being different from the template; and
after the first portal dose image is received, using the one or more evaluation parameters and the one or more evaluation criteria from the template by the processor to evaluate the first portal dose image.

53. The computer product of claim 52, wherein the first portal dose image is evaluated during an operation of a treatment radiation machine.

54. The computer product of claim 52, wherein the first portal dose image is evaluated while a treatment radiation machine is in a stand-by mode.

55. The computer product of claim 52, wherein the template prescribes multiple dose image tests be performed.

56. The computer product of claim 55, wherein the multiple dose image tests comprise (1) an area gamma test, (2) a maximum gamma test, (3) an average gamma test, (4) a gamma test with respect to a largest connected area (LCA), (5) a maximum dose difference value test, (6) an average dose difference value test, or (7) any combination of the foregoing.

57. The computer product of claim 52, wherein the template prescribes an area dose difference test be performed.

58. The computer product of claim 52, wherein the template prescribes multiple tests to be performed to evaluate the first portal dose image.

59. The computer product of claim 52, wherein the process further comprises outputting multiple test results for the first portal dose image based on the template.

60. The computer product of claim 52, wherein the act of using the processor to evaluate the first portal dose image comprises using the processor to evaluate different aspects of the first portal dose image.

61. The computer product of claim 52, wherein the act of using the processor to evaluate the first portal dose image comprises determining if at least one of the one or more evaluation parameters satisfies at least one of the one or more evaluation criteria.

62. The computer product of claim 52, wherein the one or more evaluation parameters comprise multiple evaluation parameters, and the one or more evaluation criteria comprise multiple evaluation criteria for the respective multiple evaluation parameters; and
wherein the act of using the processor to evaluate the first portal dose image comprises determining if the multiple evaluation parameters satisfy the multiple evaluation criteria, respectively.

* * * * *